(12) United States Patent
Girouard

(10) Patent No.: US 12,303,141 B2
(45) Date of Patent: May 20, 2025

(54) DISTAL FEMUR ALIGNMENT SYSTEM

(71) Applicant: Aesculap AG, Tuttlingen (DE)

(72) Inventor: Christophe Girouard, Sarcicourt (FR)

(73) Assignee: Aesculap AG, Tuttlingen (DE)

( * ) Notice: Subject to any disclaimer, the term of this patent is extended or adjusted under 35 U.S.C. 154(b) by 280 days.

(21) Appl. No.: 18/030,134

(22) PCT Filed: Oct. 14, 2021

(86) PCT No.: PCT/EP2021/078400
§ 371 (c)(1),
(2) Date: Apr. 4, 2023

(87) PCT Pub. No.: WO2022/084130
PCT Pub. Date: Apr. 28, 2022

(65) Prior Publication Data
US 2023/0371959 A1    Nov. 23, 2023

(30) Foreign Application Priority Data
Oct. 19, 2020   (EP) ..................................... 20202637

(51) Int. Cl.
*A61B 17/15*    (2006.01)
(52) U.S. Cl.
CPC .................................. *A61B 17/155* (2013.01)
(58) Field of Classification Search
CPC .................................................. A61B 17/155
See application file for complete search history.

(56) References Cited

U.S. PATENT DOCUMENTS 5,484,446 A * 1/1996 Burke .................. A61B 17/154
606/86 R
5,562,674 A * 10/1996 Stalcup ................ A61B 17/155
606/88

(Continued)

FOREIGN PATENT DOCUMENTS

| GB | 2495775 A | 4/2013 |
|---|---|---|
| WO | 2009006741 A1 | 1/2009 |
| WO | 2017108776 A1 | 6/2017 |

OTHER PUBLICATIONS

Search Report received in European Application No. 202026373.3-1122 dated Mar. 4, 2021, 7 pages.

(Continued)

*Primary Examiner* — David W Bates
(74) *Attorney, Agent, or Firm* — Christopher A. Rothe; CM Law

(57) ABSTRACT

A distal femur alignment system includes a resection guide, in particular a cutting guiding block, for guiding a resection cutting instrument, and an adjustment device for adjusting the resection guide which is adapted to be temporarily fixed to a femur. The adjustment device includes an angle adjustment module for adjusting an angle between the resection guide and the femur and a height adjustment module for adjusting a cutting height between the resection guide and the femur. The angle adjustment module and the height adjustment module each include a manually operable user adjustment element. The user adjustment elements are supported on and rotatable about a common rotation axis so as to be separately and independently operable for angle adjustment and height adjustment.

15 Claims, 3 Drawing Sheets

(56) References Cited

U.S. PATENT DOCUMENTS

| | | | | |
|---|---|---|---|---|
| 5,624,444 A * | 4/1997 | Wixon | | A61B 17/155 606/88 |
| 5,693,048 A * | 12/1997 | Stalcup | | A61B 17/155 606/86 R |
| 5,776,137 A * | 7/1998 | Katz | | A61B 17/155 606/88 |
| 5,830,216 A * | 11/1998 | Insall | | A61B 17/155 606/88 |
| 6,193,723 B1 * | 2/2001 | Cripe | | A61B 17/1764 606/88 |
| 9,314,282 B2 * | 4/2016 | Kecman | | A61B 17/155 |
| 10,034,672 B2 * | 7/2018 | Jones | | A61B 17/155 |
| 2005/0187560 A1 * | 8/2005 | Dietzel | | A61B 17/155 606/102 |
| 2007/0233140 A1 | 10/2007 | Metzger et al. | | |
| 2009/0125029 A1 * | 5/2009 | Seo | | A61B 17/155 606/88 |
| 2009/0125114 A1 * | 5/2009 | May | | A61F 2/38 623/20.14 |
| 2009/0143783 A1 * | 6/2009 | Dower | | A61B 90/06 606/88 |
| 2010/0094301 A1 * | 4/2010 | Dees | | A61B 17/155 606/89 |
| 2013/0158556 A1 * | 6/2013 | Jones | | A61B 17/1764 606/87 |
| 2019/0110907 A1 * | 4/2019 | Yoko | | A61F 2/3859 |
| 2019/0150947 A1 * | 5/2019 | Weiss | | A61B 17/142 |
| 2023/0218306 A1 * | 7/2023 | Vouaux | | A61B 17/157 606/88 |

OTHER PUBLICATIONS

Search Report received in International Application No. PCT/EP2021/078400 dated Nov. 30, 2021, 4 pages.

Written Opinion received in International Application No. PCT/EP2021/078400 dated Nov. 30, 2021, 5 pages.

* cited by examiner

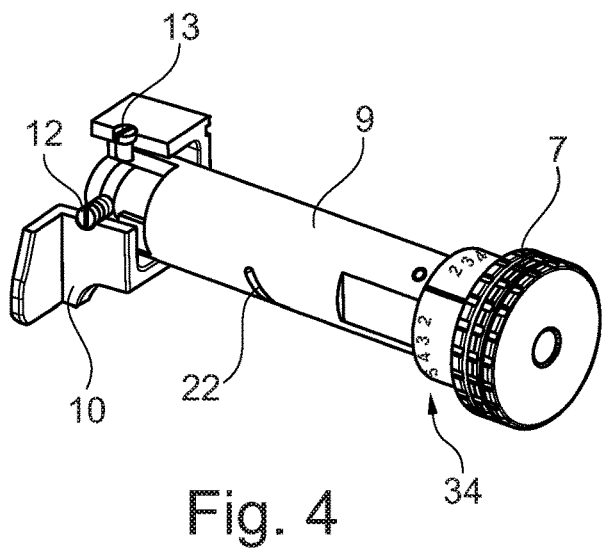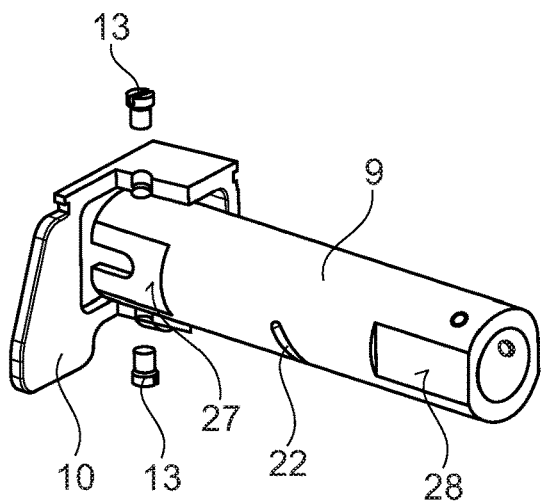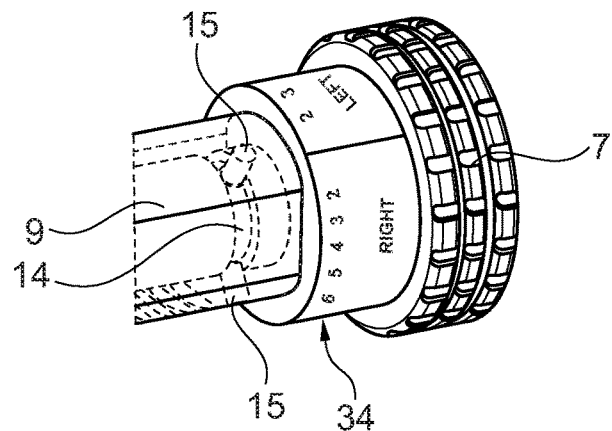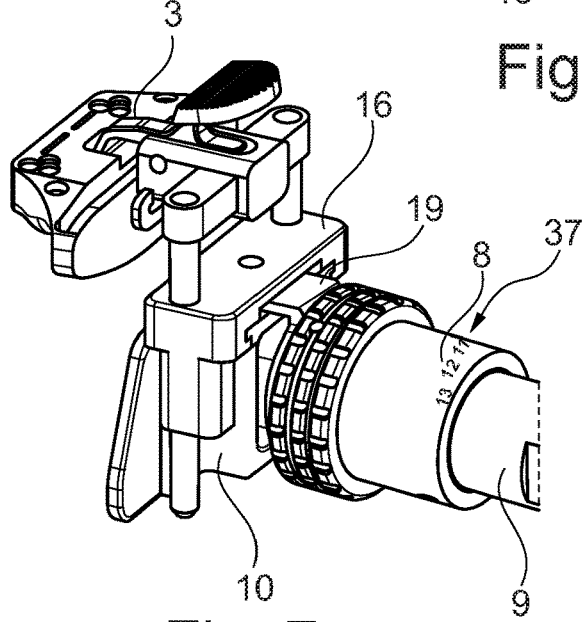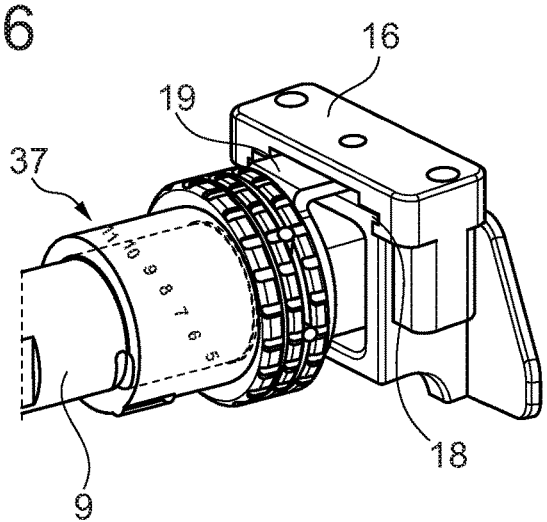

DISTAL FEMUR ALIGNMENT SYSTEM

CROSS-REFERENCE TO RELATED APPLICATIONS

This application is the United States national stage entry of International Application No. PCT/EP2021/078400, filed Oct. 14, 2021, and claims priority to European Application No. 20202637.3, filed Oct. 19, 2020. The contents of International Application No. PCT/EP2021/078400 and European Application No. 20202637.3 are incorporated by reference herein in their entireties.

FIELD

The disclosure concerns joint arthroplasty, especially knee arthroplasty and total knee arthroplasty. More specifically, the disclosure concerns devices which enable the surgeon to efficiently and accurately adjust a femur implant in reference to an intramedullary channel of a femur. In particular, the disclosure relates to a distal femur alignment/adjustment system/device/instrument (hereinafter also referred to as alignment system or alignment instrument).

BACKGROUND

The knee joint enables a person's leg to flex or articulate during movement. At the knee, a lower bone (tibia) meets an upper bone (femur). Proximate the knee, the femur has two projections known as femoral condyles. Femoral condyles engage fibrocartilage at the upper end of the tibia. The knee joint is held together by ligaments, capsule, muscle, and tendons. The knee joint may be rendered nearly or totally inoperative by extended and heavy use, disease, or trauma. Often, the best therapy is total replacement (arthroplasty). During total knee arthroplasty, the femoral and tibial surfaces joined at the knee are totally replaced.

The first step in this process is the removal of the condylar surfaces and some underlying portions thereof. The distal end of the femur is resected to provide clearance for a femoral prosthetic component. Similarly, a proximal portion of the tibia is resected to provide a flat surface for a tibial prosthetic component. A person's weight is transferred from the head of the femur proximate the hip to the ankle. Proper alignment of the knee must be maintained when femoral and tibial prosthetic implants are installed to allow the proper transfer of weight to continue. In order for the prostheses to function properly, femoral and tibial surfaces arising from these resections must be correctly aligned. For correct alignment of the femur implant, the resection of the femur's distal end is guided by a distal femur alignment system allowing the operator to adjust a desired distal cutting height and a desired Varus/Valgus angle.

For example, WO 2009/006741 A1 discloses a distal femur alignment system comprising a resection guide for guiding a resection cutting instrument and an adjustment device for adjusting the resection guide which is adapted to be temporarily fixed to a femur and comprises an angle adjustment module for adjusting an angle between the resection guide and the femur as well as a height adjustment module for adjusting a cutting height between the resection guide and the femur.

In known distal femur alignment systems, there is one module for adjusting the cutting height and another module for adjusting the Varus/Valgus angle. In known systems, the height module and the angle module are arranged at different places, e.g., arranged one above the other, causing the operator to carry out the adjustment at two different locations. Further, known distal femur alignment systems are bulky and unhandy/non-practical.

SUMMARY

Thus, there may be a need for an enhanced distal femur alignment system having a compact and reduced structure allowing the operator to perform the adjustment of the cutting height and the angle easily and intuitively.

The distal femur alignment system comprises a resection guide, in particular a cutting guiding block, for guiding a resection cutting instrument and an adjustment device for adjusting the resection guide, in particular the cutting guiding block, which is adapted to be temporarily fixed to a femur and comprises an angle adjustment module for adjusting an angle between the resection guide and the femur as well as a height adjustment module for adjusting a cutting height between the resection guide and the femur, therefor the angle adjustment module and the height adjustment module each comprising a manually operable (rotatable) user adjustment element (wheel), wherein the adjustment user adjustment elements (wheels) are supported on and rotatable about a common rotation axis so as to be separately and independently operable (rotatable) for angle adjustment and height adjustment. This has the advantage that, due to the common rotation axis, the angle user adjustment element and the height user adjustment element are/can be arranged coaxially. Thus, a compact adjustment device is provided. The setting of the angle and the height can be carried out in the same location and in the same way, namely by turning. Further, the reading of the adjusted setting can also be designed intuitively and clearly.

In other words, the distal femur alignment system is for adjusting a distal femoral resection cutting instrument in reference to a femur. The cutting instrument may be formed as a saw blade or the like. The distal femur alignment system comprises a resection guide (cutting guiding block) for guiding the distal femoral resection cutting instrument. The resection guide may comprise a cutting contour, e.g., a slit, for guiding the cutting instrument along a distal femoral cutting plane extending substantially in a transverse direction of the femur. The distal femur alignment system comprises an adjustment device for adjusting the resection guide relative to the femur. The adjustment device is adapted to be connected to the femur, preferably by an alignment rod which is fixed to an anatomical axis/intramedullary channel of the femur. The adjustment device comprises an angle adjustment module/device for adjusting an angle between the anatomical axis and the resection guide (and thus, the cutting plane) as well as a height adjustment module/device for adjusting a cutting height (distal resection amount) of the resection guide (and thus, the cutting plane) relative to a distal surface of the femur. That is, the angle adjustment module sets a Varus/Valgus angle and the height adjustment module sets a distance between the distal femoral cutting plane and the distal surface (condylar surface) of the femur. The angle adjustment module has an angle user adjustment element (functionally) connected/coupled to the resection guide such that a rotation of the angle user adjustment element relative to the resection guide about a first rotation axis, that is a longitudinal axis of the angle user adjustment element, is converted into a pivoting/rotating movement of the resection guide relative to the anatomical axis about a pivot axis. The pivot axis is preferably perpendicular to the first rotation axis. The height adjustment module has a height user adjustment element (functionally) connected/ coupled to the resection guide such that a rotation of the height user adjustment element relative to the resection guide about a second rotation axis, that is a longitudinal axis of the height user adjustment element, is converted into a translational movement of the resection guide relative to the femur, in particular into a sliding movement relative to the distal surface along a sliding axis corresponding to the second rotation axis. Thus, the angle adjustment and the height adjustment can be individually set by turning the corresponding (angle/height) user adjustment element. According to the present disclosure, the adjustment is configured in such a way that the first rotation axis coincides with the second rotation axis.

Thus, the adjustment device has a common rotation axis for adjusting, namely setting and reading, the angle and the height. In particular, the rotation axis corresponds to the anatomical axis A such that the angle user adjustment element and the height user adjustment element are arranged coaxially to each other and to the alignment rod/the anatomical axis. Thus, a radial and/or axial nesting/stacking of the two adjustment modules can be achieved. In other words, the adjustment device integrates the angle adjustment module and the height adjustment module into a common module while allowing independent/individually adjustment of the angle and the height.

According to a preferred embodiment, the angle user adjustment element and the height user adjustment element may be arranged one behind the other on the rotation axis, that is, axially stacked, preferably axially distanced to each other. Thus, a locking mechanism can be arranged in-between.

According to a preferred embodiment, the adjustment device may comprise a locking mechanism adapted to lock and unlock rotatable movement of the angle user adjustment element and/or the height user adjustment element relative to the resection guide about the rotation axis. The locking mechanism may be arranged axially between the angle user adjustment element and the height user adjustment element. The locking mechanism may comprise an operation handle (/pusher/sleeve) being switchable between a locked position in which rotatable movement of the angle user adjustment element and the height user adjustment element is restricted, an angle position in which rotatable movement of the angle user adjustment element is enabled and rotatable movement of the height user adjustment element is restricted, and a height position in which rotatable movement of the height user adjustment element is enabled and rotatable movement of the angle user adjustment element is restricted. In other words, the adjustment device is provided with a secure position avoiding accidentally change of settings. During the setting of one of the adjustments, the other one is locked to avoid mistakes. Thus, unintentional adjustment can be prevented. For example, the adjustment device may have a first (outer) contour on a (outer) circumferential surface thereof and the height user adjustment element may have a first (inner) contour on a (inner) circumferential surface thereof engaging in the first (outer) contour in a rotation-locked manner in the angle position and the locked position. Accordingly, the adjustment device may have a second (outer) contour on a (outer) circumferential surface thereof and the angle user adjustment element may have a second (inner) contour on a (inner) circumferential surface thereof engaging in the second (outer) contour in a rotation-locked manner in the height position and the locked position.

In particular, the operation handle may be axially movable (along the longitudinal axis of the operation handle, preferably corresponding to the anatomical axis) relative to the angle user adjustment element and the height user adjustment element to be switched between the locked position, the angle position and the height position. In other words, translation of the operation handle unlocks the corresponding rotatable movement. Thus, an easy locking mechanism is provided. More preferably, the operation handle may comprise an angle arrow indicating the direction of switching the operation handle for unlocking the angle adjustment and/or a height arrow indicating the direction of switching the operation handle for unlocking the height adjustment.

According to the preferred embodiment, the locked position may be arranged between the angle position and the height position. In other words, the operation handle may be moved along the longitudinal axis thereof for switching and depending on the direction of moving the angle user adjustment element or the height user adjustment element is unlocked. Thus, a common, space-saving locking mechanism is provided for both adjustments enabling the same way to be operated.

According to the preferred embodiment, the locking mechanism may comprise a release element adapted to lock and unlock the switching movement of the operation handle. Preferably, the release element may be adapted to be pressed manually, preferably against the force of a spring, by a user to enable switching, in particular axially movement, of the operation handle relative to the angle user adjustment element and the height user adjustment element. In particular, the release element may be a button on a circumference of the operation handle.

Preferably, the locking mechanism may comprise a plurality of angle engaging elements each forming an adjusted/locking angle position. The angle engaging elements may be distanced from each other, in particular in circumferential direction of the operation handle, preferably such that two adjacent locking positions generate a constantly stepwise, more preferably in 1° steps, pivoting movement between the resection guide relative to the anatomical axis. More preferably, the locking mechanism may comprise an angle limit stop limiting the adjustable angle within a predetermined range, in particular from 2° to 10° in both circumferential directions (clockwise and anti-clockwise).

According to a preferred embodiment, the adjustment device may comprise an angle scale indicating the adjusted angle of the resection guide relative to the anatomical axis. Thus, it is possible to easily read the set angle. Preferably, the angle scale may be formed by a first window in the operation handle, a first reference mark on an outer circumferential surface of the operation handle and numbers, in particular equal distanced, on an outer circumferential surface of the angle user adjustment element indicating the adjusted angle. More preferably, the numbers, apart from the number corresponding to the currently adjusted angle, are covered (not-visible) by the operation handle being in the locked position or in the height position and uncovered (visible) by the operation handle being in the angle position.

Preferably, the locking mechanism may comprise a plurality of height engaging elements each forming an adjusted/locking height position. The height engaging elements may be distanced from each other, in particular in circumferential direction of the operation handle, preferably such that two adjacent locking positions generate a constantly stepwise, more preferably in 1 mm steps, sliding movement between the resection guide relative to the distal surface. More preferably, the locking mechanism may comprise a height limit stop limiting the adjustable height within a predetermined range, in particular from 5 mm to 13 mm. Further preferably, the locking mechanism may comprise an additional height setting of 2 mm.

According to a preferred embodiment, the adjustment device may comprise a height scale indicating the adjusted cutting height of the resection guide relative to the distal surface. Thus, it is possible to easily read the set cutting height. Preferably, the height scale may be formed by a second window in the operation handle, a second reference mark on an outer circumferential surface of the operation handle and numbers, in particular helically arranged and equal distanced, on an outer circumferential surface of the height user adjustment element indicating the adjusted cutting height. More preferably, the numbers, apart from the number corresponding to the currently adjusted cutting height, are covered (not-visible) by the operation handle being in the locked position or in the angle position and uncovered (visible) by the operation handle being in the height position.

According to a preferred embodiment, the adjustment device may comprise a central pipe (/tube/sleeve) being adapted to be connected to the anatomical axis of the femur, that is, such that an angle adjustment relative to a longitudinal axis of the central pipe corresponds to an angle adjustment relative to the anatomical axis, and a femur contact plate being connected to the resection guide in such a way that the resection guide and the femur contact plate pivot together about the pivot axis and being connected to the central pipe in such a way that the central pipe and the femur contact plate are kept pivotable to each other about the pivot axis. The angle user adjustment element may be rotatably held by the central pipe about the first rotation axis and (functionally) connected/coupled to the femur contact plate such that a rotation of the angle user adjustment element relative to the central pipe is converted into a pivoting movement of the femur contact plate to the central pipe.

In particular, the angle user adjustment element may comprise a pivoting guiding groove in a circumferential surface thereof, and the femur contact plate may comprise a pivoting member received by the pivoting guiding groove. The pivoting guiding groove and the pivoting member are designed and interacting in such a way that the rotation of the angle user adjustment element pivots the femur contact plate. Preferably, the pivoting guiding groove may have a helical form, more preferably with a constant pitch. Alternatively, the pivoting guiding groove may have a depth, preferably constantly, increasing or decreasing along its circumferential extension. Preferably, the pivoting member may be fixed at the inner side of the femur contact plate and may extend radially inwards. In particular, the pivoting member may be formed as a spherical pin with the longitudinal axis thereof being perpendicular to the pivot axis and the first rotation axis. For example, the pivoting member may contact a circumferential surface of the angle user adjustment element and thus, guide and/or control the pivoting movement.

In particular, the adjustment device may comprise a support member supporting the femur contact plate pivotably on the central pipe about the pivot axis, a longitudinal axis of the support member corresponding to the pivot axis. The support member may be fixed at the inner side of the femur contact plate and may extend radially inwards. Preferably, the support member may be formed by a pin, for example two pins being arranged on opposite sides in a circumferential direction of the central pipe, engaging in a corresponding hole in the circumferential surface of the central pipe, for example two holes being arranged on opposite sides in the circumferential direction.

In particular, the angle user adjustment element may comprise a rotational guiding groove in a circumferential surface thereof, and the central pipe may comprise a rotation member received by the rotational guiding groove. The rotational guiding groove and the rotation member are designed and interacting in such a way that the angle user adjustment element is freely rotatable relative to the central pipe about the rotation axis. Preferably, the rotational guiding groove may be a circumferential (annular) groove being arranged in a plane perpendicular to the rotation axis. Preferably, the rotation member may being fixed at the inner side of the central pipe and may extend radially inwards. In particular, the rotation member may be formed by a plurality of pins, the longitudinal axes of the pins being arranged in the plane perpendicular to the rotation axis. The pins may be equally distributed over the circumferential surface of the central pipe.

According to a preferred embodiment the central pipe may be adapted to be connected to the distal surface of the femur, that is, such that a height adjustment relative to the central pipe corresponds to a height adjustment to the distal surface, and the adjustment device may comprise a sliding element being connected to the resection guide in such a way that the resection guide and the sliding element slide together along the sliding axis and being connected to the central pipe in such a way that the central pipe and the sliding element are kept slidable to each other along the sliding axis. The height user adjustment element may be rotatably held by the sliding element about the second rotation axis and (functionally) connected/coupled to the resection guide such that a rotation of the height user adjustment element relative to the resection guide about the second rotation axis is converted into a sliding movement of the resection guide relative to the central pipe along the sliding axis.

In particular, the central pipe may comprise a sliding guiding groove in a circumferential surface thereof, and the height user adjustment element may comprise a sliding member received by the sliding guiding groove. The sliding guiding groove and the sliding member are designed and interacting in such a way that the rotation of the height user adjustment element slides the sliding element along the sliding axis. Preferably, the sliding guiding groove may have a helical form (may be helicoidal), preferably with a constant pitch. Preferably, the sliding member may formed as a spherical pin with the longitudinal axis thereof being perpendicular to the sliding axis. Preferably, the sliding member may be fixed at the inner side of the height user adjustment element and may extend radially inwards.

In particular, the sliding element may comprise a coupling member connected to the femur contact plate in such a way that the coupling member and the femur contact plate pivot together and are slidable relative to each. Preferably, the coupling member may comprise a guiding element, preferably a straight projection or groove, and the femur contact plate may comprise a guiding member, preferably a straight groove or projection, receiving the guiding element. The guiding element and the guiding member may extend along the longitudinal axis of the femur contact plate. Thus, a linear bearing/one-directionally bearing is provided, excluding the coupling member and the femur contact plate to pivot relative to each other.

In particular, the sliding element may comprise a ring member connected to the coupling member in such a way that the ring member and the coupling member slide together and are pivotable relative to each. Preferably, the ring member may comprise an elongated hole elongated in a direction perpendicular to the sliding axis, and the coupling member may comprise a projection received by the oblong hole. The elongated hole may be designed so as to allow maximal pivoting movement of the femur contact plate relative to the central while attached the member and the coupling member so as to slide together. Thus, the pivotability is not impeded by the sliding element.

In particular, the sliding element, especially the ring member, may comprise a rotational guiding groove in a circumferential surface thereof, and the height user adjustment element may comprise a rotation member received by the rotational guiding groove. The rotational guiding groove and the rotation member are designed and interacting in such a way that the height user adjustment element is freely rotatable relative to the sliding element about the rotation axis. Preferably, the rotational guiding groove may be a circumferential (annular) groove being arranged in a plane perpendicular to the rotation axis. Preferably, the rotation member may being fixed at the inner side of the central pipe and may extend radially inwards. In particular, the rotation member may be formed by a plurality of pins, the longitudinal axes of the pins being arranged in the plane perpendicular to the rotation axis. The pins may be equally distributed over the circumferential surface of the central pipe.

In other words, the present disclosure is directed to a distal femur alignment system allowing to adjust the Varus/Valgus angle, preferably from 2° to 10° with a 1° increment, and the cutting height, preferably to 9 mm±4 mm with a 1 mm increment and an additional setting 2 mm, and thus, to manage an ideal femur alignment in reference to an anatomical axis. In contrast to current systems having a first adjustment module for the distal cut height setting and reading and a second adjustment module for the Varus/Valgus angle setting and reading, the distal femur alignment system allows the setting of both adjustment in the same way by turning a wheel, in the same location (along the anatomical axis/intramedullary axis/rod) with a secure position avoiding accidentally change of the settings. Due to the common location, the manipulation/setting/adjusting and the settings reading are improved compared to the existing systems using two different/independent modules arranged separately.

In the distal femur alignment system, each planned setting can be reached easily by turning the corresponding user adjustment element (wheel) after unlocking a central locking button, by moving the central button in a described direction. During the setting of one of the adjustments, the other one is locked in order to avoid mistakes. E.g. for Varus/Valgus adjustment, first, the locking button is pressed to unlock an operating handle, second, the operating handle is translated from a neutral position in a desired direction to unlock the Varus/Valgus wheel, third, the Varus/Valgus wheel is turned to set the Varus/Valgus angle and an arrow indicates the new adjusted angle, last the locking button is pressed to put the operation handle back into the neutral position and the set value is locked and appears in a window of the operation handle. The advantages are the setting of both adjustments in an unique module, the reading of both settings in an unique module, the neutral position to lock both adjustments at the same time and the same way of reaching the settings by turning a wheel.

In the distal femur alignment system, the angle user adjustment element (button/angle wheel) allows to connect the distal femur alignment system with the intramedullary axis through the intramedullary/alignment rod. The angle is managed by rotation/pivoting of the femur contact plate around the supporting member (pins). The rotation is generated by the handling of the angle wheel. The rotation of the angle wheel generates the angulation of the femur contact plate thanks to the connection between the spherical axis of the pivoting member and the helicoidal groove of the angle wheel. The cutting height is managed by sliding of the sliding part on the femur contact plate. The resection guide and its support are connected to the sliding part thanks to two rods. The sliding is generated by the height user adjustment element (button/height wheel) linked to the sliding part through the ring part. The locking button is used to choose the position (neutral, angle setting, height setting) of the distal femur alignment system, in particular the operation handle, thanks to three specific grooves in the central pipe. The distal femur alignment system is automatically locked in the desired position thanks to a spring after releasing the locking button.

The Varus/Valgus is the angle between the (femur) anatomic axis and the line perpendicular to the femur distal cut. In the angle adjustment, the central pipe is connected to the femur contact plate by two pins allowing the rotation for angle setting. The angle is generated by turning the angle wheel thanks to a helicoidal groove on the angle wheel's end and a spherical axis fixed to the femur contact plate. The angle wheel is connected to the central pipe by three pins. In the height adjustment, the height wheel is connected to the central pipe thanks to a pin inside a helicoidal groove allowing the translation of the height wheel when turning along the central pipe. The ring part is connected to the height wheel by three pins. The ring part is connected to the sliding part that is able to translate along the femur contact plate allowing the setting of the distal femur cutting height. The femur distal cutting guide and its support are connected to the sliding part thanks to two rods.

BRIEF DESCRIPTION OF THE DRAWINGS

The present disclosure is explained in more detail below on the basis of a preferred embodiment using figures. The figures are of a schematic nature and intended to improve the understanding of the disclosure. Same elements are referenced to with the same reference signs.

FIGS. 4 to 6 are perspective views of details of an angle adjustment module of the distal femur alignment system;

FIGS. 7 to 9 are perspective views of details of a height adjustment module of the distal femur alignment system.

DETAILED DESCRIPTION

Figure 1:
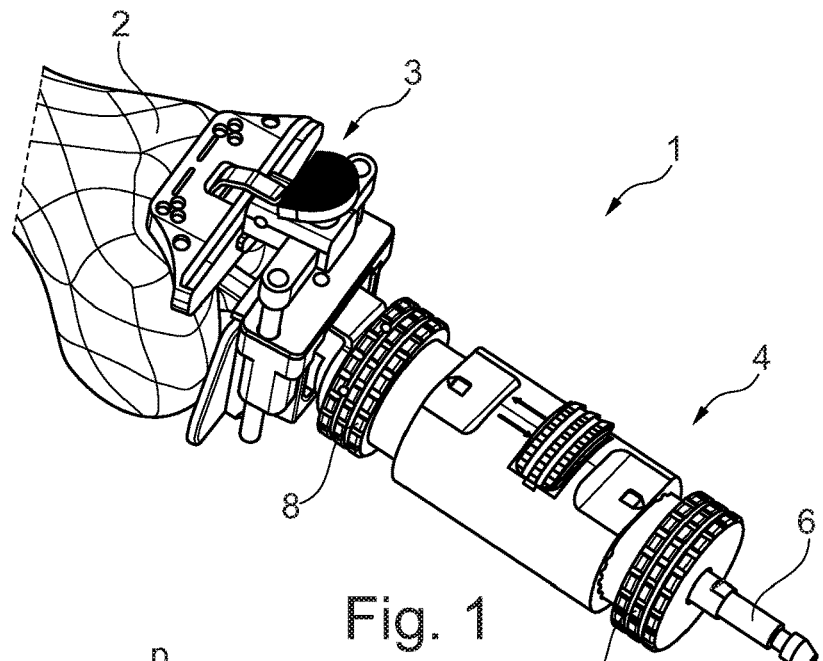
FIG. 1 is a perspective view of a distal femur alignment system.
Figure 2:
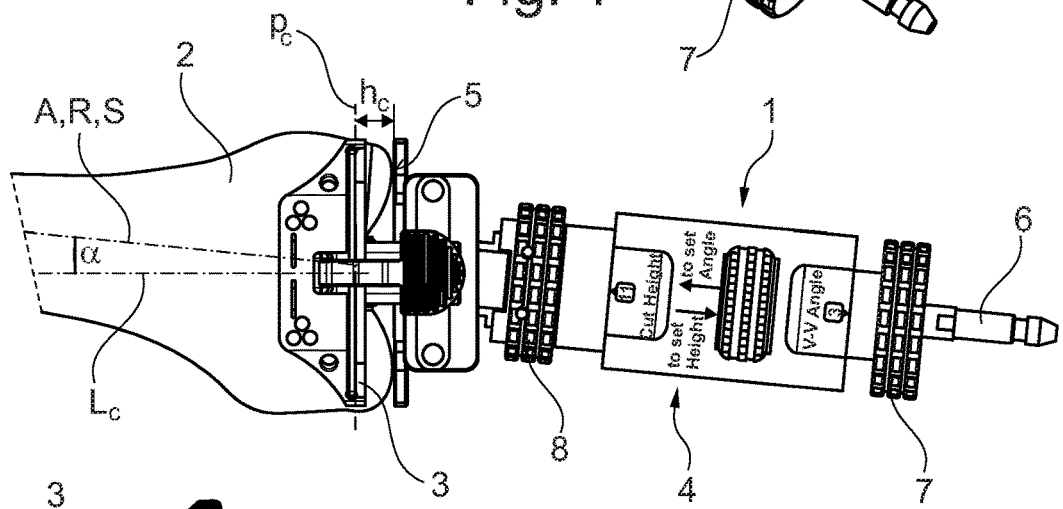
FIG. 2 is a top view from above of the distal femur alignment system.
Figure 3:
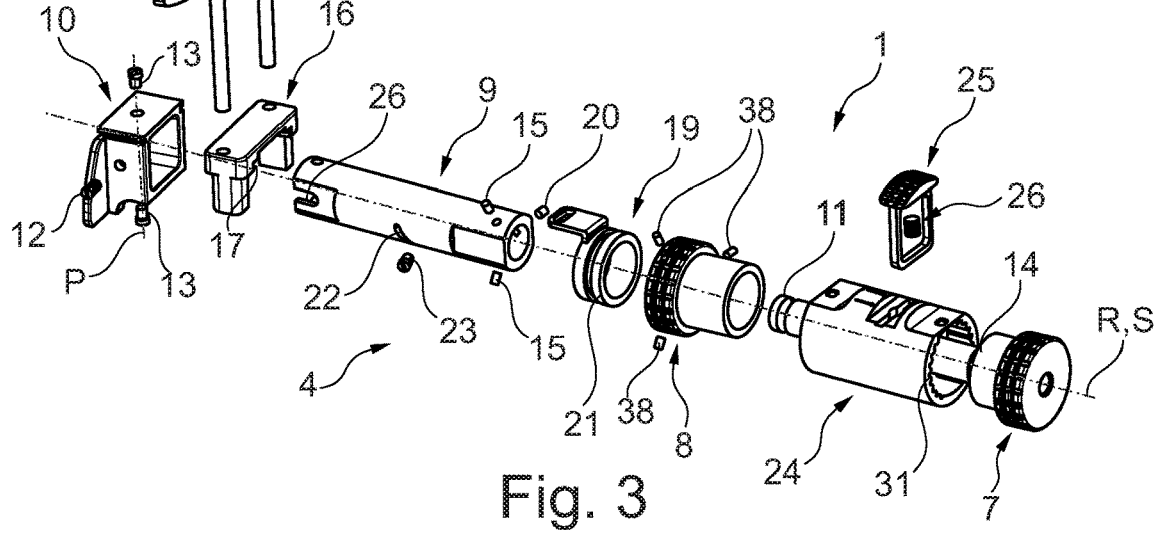
FIG. 3 is an exploded view of the distal femur alignment system.

FIGS. 1 to 3 show a preferred embodiment of a distal femur alignment/adjustment system/instrument 1 (hereinafter referred to as alignment system 1) of the present disclosure. The alignment system 1 is for adjusting a (not shown) distal femoral resection cutting instrument (hereinafter referred to as cutting instrument) in reference to a femur 2. The cutting instrument may be formed as a saw blade or the like. The alignment system 1 comprises a resection guide 3

(cutting guiding block) for guiding the cutting instrument. The resection guide 3 may comprise a cutting contour, e.g., a slit, for guiding the cutting instrument along a distal femoral cutting plane pc extending substantially in a transverse direction of the femur 2.

The alignment system 1 comprises an adjustment device 4. The adjustment device 4 is for adjusting, in particular orientating and/or positioning, the resection guide 3 relative to the femur 2. In particular, the adjustment device 4 is for orientating an angle α between the femur 2, e.g., an anatomical axis/an intramedullary axis/channel A thereof, and the resection guide 3, e.g. a line Lc perpendicular to the distal femoral cutting plane pc guided by the resection guide 3. That is, the adjustment device 4 is for orientating a varus/valgus angle. In particular, the adjustment device 4 is for positioning a cutting height (distal resection amount) hc of the resection guide 3 relative to the femur 3, preferably between the distal femoral cutting plane pc and a distal surface (condylar surface) 5 of the femur 2. The adjustment device 4 is adapted to be attached/connected to the femur 2, in particular statically. Preferably, the adjustment device 4 is attached to the femur 2 by an alignment rod 6. The alignment rod 6 may be fixedly attached to the femur 2, preferably in such a way that a longitudinal axis of the alignment rod 6 coincides with the anatomical axis A the femur 2.

The adjustment device 4 comprises an angle adjustment module/device/unit for adjusting/orientating the angle α. The angle adjustment module has an angle user adjustment element 7 (hereinafter referred to as an angle wheel 7) (functionally) connected/coupled to the resection guide 3 such that a rotation of the angle wheel 7 relative to the resection guide 3 (via a transmission) about a first rotation axis is converted into a pivoting movement of the resection guide 3 relative to the anatomical axis A about a pivot axis P, preferably the pivot axis P being perpendicular to the first rotation axis. The adjustment device 4 comprises a height adjustment module/device/unit for adjusting/positioning the cutting height hc. The height adjustment module has a height user adjustment element 8 (hereinafter referred to as a height wheel 8) (functionally) connected/coupled to the resection guide 3 (via a transmission) such that a rotation of the height wheel 8 relative to the resection guide 3 about a second rotation axis is converted into a translational/sliding movement of the resection guide 3 relative to the distal surface 5 along a sliding axis S corresponding to the second rotation axis.

In other words, the distal femur alignment system 1 comprises a resection guide 3, in particular a cutting guiding block 3, for guiding a resection cutting instrument and an adjustment device 4 for adjusting the cutting guiding block 3 which is adapted to be temporarily fixed to a femur 2 and comprises an angle adjustment module for adjusting an angle α between the cutting guiding block 3 and the femur 2 as well as a height adjustment module for adjusting a cutting height hc of the resection guide 3 between the cutting guiding block 3 and the femur 2, therefor the angle adjustment module and the height adjustment module each comprising a manually operable user adjustment element 7, 8, characterized in that, the user adjustment elements 7, 8 are supported on a common rotation axis R so as to be separately and independently operable for angle adjustment and height adjustment.

In the adjustment device 4, the first rotation axis coincides with the second rotation axis, that is, a common rotation axis R. That is, the angle wheel 7 and the height wheel 8 are arranged coaxially. Thus, the adjusting/setting of the angle α and the cutting height hc can be carried out in the same location and in the same way, namely by turning the angle wheel 7 and the height wheel 8 independent and separate from each other about the rotation axis R, respectively. In particular, the rotation axis R corresponds to the anatomical axis A. That is, the angle wheel 7 is arranged coaxially to the alignment rod 6/the anatomical axis A. That is, the height wheel 8 is arranged coaxially to the alignment rod 6/the anatomical axis A.

In the following, the adjustment device 4 is described in detail with reference to FIG. 3. The adjustment device 4 comprises a central pipe 9. The central pipe 9 is adapted to be (preferably statically) connected to the femur 2, preferably such that a longitudinal axis of the central pipe corresponds to the anatomical axis A. The central pipe 9 may be connected to the femur 2 through the alignment rod 6. For example, the central pipe 9 may be held coaxially on the alignment rod 3 by the angle wheel 7.

The angle adjustment module is illustrated in detail in FIGS. 4 to 6. The adjustment device 4 comprises a (femur/distal) contact plate 10. Preferably, the contact plate 10 is adapted to contact the distal surface 5 of the femur 2. The contact plate 10 may be connected to the resection guide 3 in such a way that the contact plate 10 and the resection guide 3 pivot (or rotate) together about the pivot axis P. The contact plate 10 may be connected to the central pipe 9 so that the contact plate 10 and the central pipe 9 are kept relatively pivotable to each other, that is, pivot (or rotate) relative to each other about the pivot axis P. The angle wheel 7 may be rotatably held by the central pipe 9 about the rotation axis R. Hence, the angle wheel 7 is (functionally) connected/coupled to the contact plate 10 such that a rotation of the angle wheel 7 relative to the central pipe 9 is converted into the pivoting movement of the contact plate 10 (together with the resection guide 3) relative to the central pipe 9 (and thus, relative to the anatomical axis A) about the pivot axis P.

In particular, the angle wheel 7 comprises a pivoting guiding groove 11 in a circumferential surface thereof. The contact plate 10 comprises a pivoting member 12 received by the pivoting guiding groove 11. The pivoting member 12 may be fixed at the inner side of the contact plate 10 and extend radially inwards. The pivoting guiding groove 11 and the pivoting member 12 are designed and interacting in such a way that the rotation of the angle wheel 7 pivots the contact plate 10. Preferably, the pivoting guiding groove 11 may have a helical form (may be helicoidal), preferably with a constant pitch. Alternatively, the pivoting guiding groove 11 may have a depth, preferably constantly, increasing or decreasing along its circumferential extension. Preferably, the pivoting member 12 may be formed as a spherical pin. In particular, a longitudinal axis of the pivoting member 12 may be perpendicular to the rotation axis R and the pivot axis P. The pivoting member 12 passes through an oblong cut out in a circumferential surface of the central pipe 9. The cut out is elongated in a direction parallel to the rotation axis enabling the pivoting member 12 and the contact plate 10 to pivot.

The adjustment device 4 comprises a support member 13 supporting the contact plate 10 pivotably on the central pipe 9 about the pivot axis P. A longitudinal axis of the support member 13 corresponds to the pivot axis P. The support member 13 may be formed by a pin, preferably two pins being arranged on opposite sides in a circumferential direction of the central pipe 9, engaging in a corresponding hole in the circumferential surface of the central pipe 9, preferably two holes being arranged on opposite sides in the circumferential direction. The support member 13 may be fixed at the inner side of the contact plate 10 and extend radially inwards.

In particular, the angle wheel 7 comprises a rotational guiding groove 14 in a circumferential surface thereof. The central pipe 9 comprises a rotation member 15 received by the rotational guiding groove 14. The rotation member 15 may be fixed at the inner side of the central pipe 9 and extend radially inwards. The rotational guiding groove 14 and the rotation member 15 are designed and interacting in such a way that the angle wheel 7 is freely rotatable relative to the central pipe 9 about the rotation axis R. In particular, the rotational guiding groove 14 may be circumferential (annular) groove being arranged in a plane perpendicular to the rotation axis R. A longitudinal axis of the rotation member 15 is arranged in the plane perpendicular to the rotation axis R. In particular, the rotation member 15 may be formed by a pin, preferably by a plurality of pins, the longitudinal axes of the pins being arranged in the plane perpendicular to the rotation axis R. The plurality of pins may be equally distributed over the circumferential surface of the central pipe 9.

Figure 9:
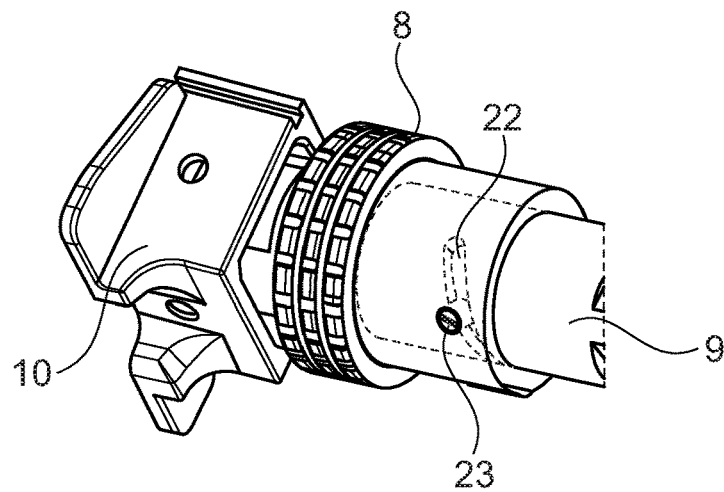

The height adjustment module is illustrated in detail in FIGS. 7 to 9. The adjustment device 4 comprises a sliding element. The sliding element may be connected to the resection guide 3 in such a way that the sliding element and the resection guide 3 slide/move/translate together along the sliding axis S. In particular, the sliding element comprises a coupling member 16 connected to the contact plate 10 in such a way that the coupling member 16 and the contact plate 10 pivot together and are slidable relative to each. The resection guide 3 may comprise a support rod, preferably two support rods, received by a corresponding hole, preferably two holes, in the coupling member 16 and, for example, extending in a direction parallel to the pivot axis P.

The sliding element (coupling member 16) may be connected to the central pipe 9 in such a way that the sliding element and the central pipe 9 are kept slidable to each other, that is, slide relative to each other along the sliding axis S. The coupling member 16 may comprise a guiding element 17, preferably a straight projection or groove. The contact plate 10 may comprise a guiding member 18, preferably a straight groove or projection, receiving the guiding element 17. The guiding element and the guiding member extend along the longitudinal axis of the femur contact plate. Alternatively, the guiding element 17 may be formed by the central pipe 9 or any part being moving translatorically together with the alignment rod 6.

The height wheel 8 is functionally connected to the resection guide 3 (by the sliding element) such that a rotation of the height wheel 8 relative to the central pipe 9 is converted into sliding movement of the sliding element 16 relative to the central pipe 9. In particular, the sliding element comprises a ring member 19 connected to the coupling member 16 in such a way that the ring member 19 and the coupling member 16 slide together and are pivotable relative to each. The ring member 19 may comprise an elongated/oblong (through) hole 20 elongated in a direction perpendicular to the sliding axis S enabling the coupling member 16 (and the resection guide 3) to pivot together with the contact plate 10. The coupling member 16 may comprise a (not shown) projection, preferably extending radially inwards, received by the elongated hole 20.

The height wheel 8 may be rotatably held by the sliding element (the ring member 19) about the rotation axis R. In particular, the ring member 19 comprises a rotational guiding groove 21 in a circumferential surface thereof. The height wheel 8 comprises a rotation member 38 received by the rotational guiding groove 21. The rotation member 38 may be fixed at the inner side of the height wheel 8 and extend radially inwards. The rotational guiding groove 21 and the rotation member 38 are designed and interacting in such a way that the height wheel 8 is freely rotatable relative to the ring member 19 about the rotation axis R. In particular, the rotational guiding groove 21 may be circumferential (annular) groove being arranged in a plane perpendicular to the rotation axis R. A longitudinal axis of the rotation member 38 is arranged in the plane perpendicular to the rotation axis R. In particular, the rotation member 38 may be formed by a pin, preferably by a plurality of pins, the longitudinal axes of the pins being arranged in the plane perpendicular to the rotation axis R. The plurality of pins may be equally distributed over the circumferential surface of the height wheel 8.

In particular, the central pipe 9 comprises a sliding guiding groove 22 in a circumferential surface thereof. The height wheel 8 comprises a sliding member 23 received by the sliding guiding groove 22. The sliding member 23 may be fixed at the inner side of the height wheel 8 and extend radially inwards. The sliding guiding groove 22 and the sliding member 23 are designed and interacting in such a way that the rotation of the height wheel 8 slides the height wheel 8 along the sliding axis S. Preferably, the sliding guiding groove 22 may have a helical form (may be helicoidal), preferably with a constant pitch. Preferably, the sliding member 23 may be formed as a spherical pin. In particular, a longitudinal axis of the sliding member 23 may be perpendicular to the sliding axis S (the rotation axis R).

The adjustment device 4 may comprise a locking mechanism for locking and unlocking the adjusting of the cutting height hc and the angle α and/or indicating the adjusted cutting height hc and angle α. The locking mechanism is illustrated in detail in FIGS. 10 to 13. In particular, the adjustment device 4 (locking mechanism) comprises an operation handle 24 (sleeve/pusher) being switchable between a locked position (neutral position), an angle position and a height position. In the locked position (FIGS. 10 and 13), a rotational/rotatable movement of the angle wheel 7 and the height wheel 8 about the rotation axis R is restricted. In the angle position (FIGS. 11 and 12), rotatable movement of the angle wheel 7 is enabled and rotatable movement of the height wheel 8 is restricted. In the height position, rotatable movement of the height wheel 8 is enabled and rotatable movement of the angle wheel 7 is restricted.

The adjustment device 4 (locking mechanism) comprises a (release) button 25 adapted to lock and unlock the switching movement of the operation handle 24. The button 25 is arranged on a circumference of the operation handle 24. The button 25 is adapted to be pressed manually by a user to switch the locking mechanism and to enable (axial) movement of the operation handle 24 between the locked position and the unlocked position (or between the unlocked position and the locked position). The adjustment device 4 comprises a spring 26 pre-tensioning the button 25 into a position in which movement of the operation handle is restricted. In particular, the button 25 may comprise an engaging member engaging into a groove or the like in the central pipe 9.

The operation handle 24 may be axially movable along the longitudinal axis of the operation handle 24, preferably corresponding to the anatomical axis A, relative to the angle wheel 7 and the height wheel 8 to be switched between the locked position, the angle position and the height position. The locked position may be arranged between the angle position and the height position. For example, the adjustment device 4 (the central pipe 9) may have a first outer contour 27 on an outer circumferential surface thereof, and the height wheel may have a (not illustrated) first inner contour on an inner circumferential surface thereof engaging in the first outer contour 27 in a rotation-locked manner in the angle position and the locked position. Accordingly, the adjustment device 4 (the central pipe 9) may have a second outer contour 28 on an outer circumferential surface thereof, and the angle wheel may have a second inner contour on an inner circumferential surface thereof engaging in the second outer contour 28 in a rotation-locked manner in the height position and the locked position. The operation handle 24 may comprise an angle arrow 29 indicating the direction of switching the operation handle 24 for unlocking the angle adjustment. The operation handle 24 may comprise a height arrow 30 indicating the direction of switching the operation handle 24 for unlocking the height adjustment.

Figure 10:
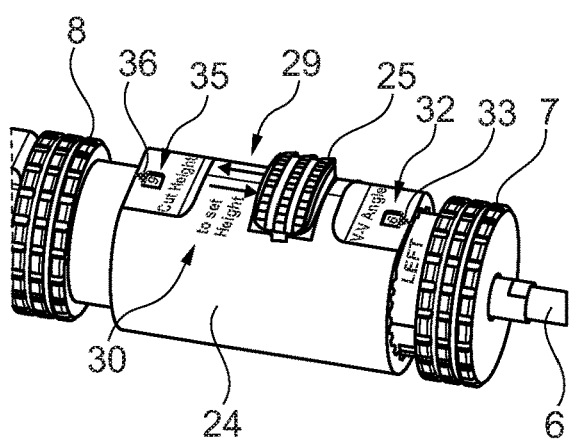
FIGS. 10 to 13 are perspective views of details of a locking mechanism of the distal femur alignment system.
Figure 11:
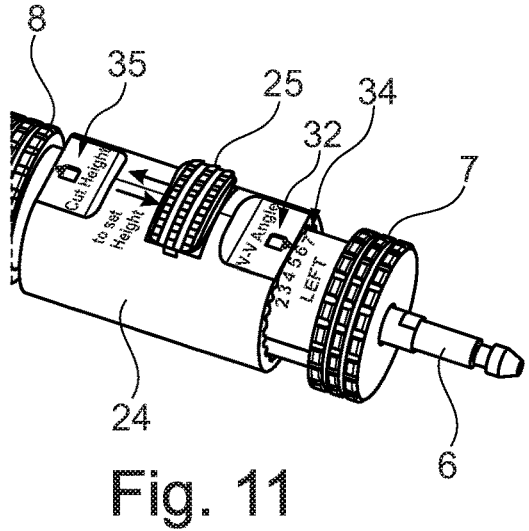
Figure 12:
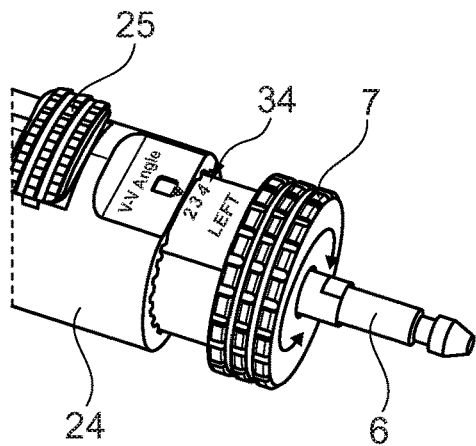
Figure 13:
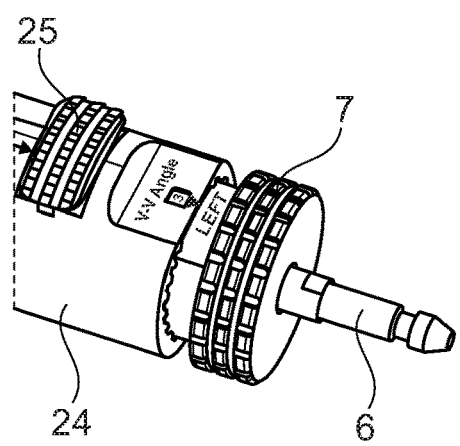

The locking mechanism (the operation handle 24) may comprise a plurality of angle engaging elements 31 each forming an adjusted/locking angle position. The angle engaging elements 31 may be formed as grooves in the inner circumferential surface operation handle 24 (FIG. 3). The angle engaging elements may be distanced from each other, in particular in circumferential direction of the operation handle, preferably such that two adjacent locking positions generate a constantly stepwise, more preferably in 1° steps, pivoting movement between the resection guide 3 relative to the anatomical axis A. The locking mechanism may comprise a (not shown) angle limit stop limiting the adjustable angle within a predetermined range, in particular from 2° to 10° in both circumferential directions (clockwise and anti-clockwise). The adjustment device 4 (locking mechanism) may comprise an angle scale indicating the adjusted angle of the resection guide 3 relative to the anatomical axis A. The angle scale may be formed by a first window 32 in the operation handle 24, a first reference mark 33 on an outer circumferential surface of the operation handle 24 and numbers 34, in particular equal distanced, on an outer circumferential surface of the angle wheel 7 indicating the adjusted angle. The numbers 34, apart from the number corresponding to the currently adjusted angle, are covered (not-visible) by the operation handle 24 being in the locked position or in the height position (FIGS. 10 and 13). The numbers 34 are uncovered (visible) by the operation handle 24 being in the angle position (FIGS. 11 and 12).

The locking mechanism (the operation handle 24) may comprise a plurality of (not shown) height engaging elements each forming an adjusted/locking height position. The height engaging elements may be distanced from each other, in particular in circumferential direction of the operation handle 24, preferably such that two adjacent locking positions generate a constantly stepwise, more preferably in 1 mm steps, sliding movement between the resection guide 3 relative to the distal surface 5. The locking mechanism may comprise a (not shown) height limit stop limiting the adjustable height within a predetermined range, in particular from 5 mm to 13 mm. The locking mechanism may comprise an additional height setting of 2 mm. The adjustment device 4 (locking mechanism) may comprise a height scale indicating the adjusted cutting height of the resection guide 3 relative to the distal surface 5. The height scale may be formed by a second window 35 in the operation handle 24, a second reference mark 36 on an outer circumferential surface of the operation handle 24 and numbers 37, in particular helically arranged and equal distanced, on an outer circumferential surface of the height wheel 8 indicating the adjusted cutting height. The numbers 37, apart from the number corresponding to the currently adjusted height, are covered (not-visible) by the operation handle 24 being in the locked position or in the angle position (FIGS. 10 to 13). The numbers 34 are uncovered (visible) by the operation handle 24 being in the height position.

The invention claimed is:

1. A distal femur alignment system, comprising:
   a resection guide, for guiding a resection cutting instrument;
   an adjustment device for adjusting the resection guide which is adapted to be temporarily fixed to a femur;
   an angle adjustment module for adjusting an angle between the resection guide and the femur; and
   a height adjustment module for adjusting a cutting height between the resection guide and the femur,
   the angle adjustment module comprising a first user adjustment element that is manually operable,
   the height adjustment module each comprising a second manually operable-user adjustment element, that is manually operable, and
   the first user adjustment element and the second user adjustment element being supported on and rotatable about a common rotation axis so as to be separately and independently operable for angle adjustment and height adjustment.

2. The distal femur alignment system according to claim 1, wherein:
   the angle adjustment module is for adjusting the angle between an anatomical axis of the femur and the resection guide,
   the first user adjustment element is coupled to the resection guide such that a rotation of the first user adjustment element relative to the resection guide about a first rotation axis is converted into a pivoting movement of the resection guide relative to the anatomical axis about a pivot axis,
   the adjustment module is for adjusting the cutting height of the resection guide relative to a distal surface of the femur,
   the second user adjustment element is coupled to the resection guide such that a rotation of the second user adjustment element relative to the resection guide about a second rotation axis is converted into a translational movement of the resection guide relative to the distal surface along a translation axis, and
   the adjustment device is configured in such a way that the first rotation axis coincides with the second rotation axis.

3. The distal femur alignment system according to claim 1, wherein the first user adjustment element and the second user adjustment element are arranged coaxially on the rotation axis.

4. The distal femur alignment system according to claim 1, wherein the adjustment device comprises a locking mechanism adapted to lock and unlock rotatable movement of the first user adjustment element and the second user adjustment element,
   the locking mechanism comprising an operation handle that is switchable between:
   a locked position in which rotatable movement of the first user adjustment element and the second user adjustment element is restricted,
   an angle position in which rotatable movement of the first user adjustment element is enabled and rotatable movement of the second user adjustment element is restricted, and a height position in which rotatable movement of the second user adjustment element is enabled and rotatable movement of the first user adjustment element is restricted.

5. The distal femur alignment system according to claim 4, wherein the operation handle is axially movable relative to the first user adjustment element and the second user adjustment element to switch the operation handle between the locked position, the angle position and the height position, the locked position being arranged between the angle position and the height position.

6. The distal femur alignment system according to claim 4, wherein the locking mechanism comprises a release element adapted to lock and unlock switching movement of the operation handle, the release element being adapted to be pressed manually by a user to enable switching of the operation handle.

7. The distal femur alignment system according to claim 4, wherein the locking mechanism comprises a plurality of angle engaging elements each forming an adjusted angle position, the angle engaging elements being distanced from each other such that two adjacent adjusted angle positions generate a constantly stepwise pivoting movement between the resection guide relative to an anatomical axis, and/or the locking mechanism comprises an angle limit stop limiting the adjustable angle within a predetermined range.

8. The distal femur alignment system according to claim 4, wherein the locking mechanism comprises a plurality of height engaging elements each forming an adjusted height position, the height engaging elements being distanced from each other such that two adjacent adjusted height positions generate a constantly stepwise sliding movement between the resection guide relative to the distal surface, and/or the locking mechanism comprises a height limit stop limiting the adjustable height within a predetermined range.

9. The distal femur alignment system according to claim 4, wherein the adjustment device comprises an angle scale indicating the adjusted angle of the resection guide relative to an anatomical axis and/or a height scale indicating the adjusted cutting height of the resection guide relative to the distal surface and/or an angle arrow indicating a direction of switching the operation handle for unlocking rotatable movement of the first user adjustment element and a height arrow indicating a direction of switching the operation handle for unlocking rotatable movement of the second user adjustment element.

10. The distal femur alignment system according to claim 1, wherein the adjustment device comprises a central pipe adapted to be connected to an anatomical axis of the femur and a femur contact plate being connected to the resection guide in such a way that the resection guide and the femur contact plate pivot together about a pivot axis and being connected to the central pipe in such a way that the central pipe and the femur contact plate are kept pivotable to each other about the pivot axis, the angle user adjustment element being rotatably held by the central pipe about the first rotation axis and functionally connected to the femur contact plate such that a rotation of the angle user adjustment element relative to the central pipe is converted into a pivoting movement of the femur contact plate relative to the central pipe.

11. The distal femur alignment system according to claim 10, wherein the first user adjustment element comprises a pivoting guiding groove in a circumferential surface of the first user adjustment element, and the femur contact plate comprises a pivoting member received by the pivoting guiding groove in such a way that rotation of the first user adjustment element.

12. The distal femur alignment system according to claim 10, wherein the central pipe is adapted to be connected to the distal surface of the femur, and the adjustment device comprises a sliding element being connected to the resection guide in such a way that the resection guide and the sliding element slide together along a sliding axis and being connected to the central pipe in such a way that the central pipe and the sliding element are kept slidable to each other along the sliding axis, the second user adjustment element being rotatably held by the sliding element about a second rotation axis and functionally connected to the resection guide such that a rotation of the second user adjustment element relative to the resection guide about the second rotation axis is converted into a sliding movement of the resection guide relative to the central pipe along the sliding axis.

13. The distal femur alignment system according to claim 12, wherein the central pipe comprises a sliding guiding groove in a circumferential surface of the central pipe and the second user adjustment element comprises a sliding member received by the sliding guiding groove in such a way that rotation of the second user adjustment element slides the sliding element along the sliding axis.

14. The distal femur alignment system according to claim 12, wherein the sliding element comprises a coupling member connected to the femur contact plate in such a way that the coupling member and the femur contact plate pivot together and are slidable relative to each other.

15. The distal femur alignment system according to claim 14, wherein the sliding element comprises a ring member connected to the coupling member in such a way that the ring member and the coupling member slide together and are pivotable relative to each other.

* * * * *